United States Patent
Bernardo et al.

(10) Patent No.: US 11,278,651 B2
(45) Date of Patent: Mar. 22, 2022

(54) MEMBRANE AND DEVICE FOR TREATING RESTLESS LEG SYNDROME

(71) Applicant: Gambro Lundia AB, Lund (SE)

(72) Inventors: Angelito A. Bernardo, River Forest, IL (US); Angela Sofia Rivera Florez, Port St. Lucie, FL (US); Lars-Goran Nilsson, Hoor (SE); Rafael Mauricio Sanabria Arenas, Bogota (CO); Alfonso Bunch Barrera, Bogota (CO)

(73) Assignee: Gambro Lundia AB, Lund (SE)

( * ) Notice: Subject to any disclaimer, the term of this patent is extended or adjusted under 35 U.S.C. 154(b) by 543 days.

(21) Appl. No.: 16/163,123

(22) Filed: Oct. 17, 2018

(65) Prior Publication Data
US 2020/0121839 A1  Apr. 23, 2020

(51) Int. Cl.
*A61M 1/16* (2006.01)
*A61P 25/00* (2006.01)
(Continued)

(52) U.S. Cl.
CPC ............ *A61M 1/16* (2013.01); *A61K 31/197* (2013.01); *A61K 31/381* (2013.01);
(Continued)

(58) Field of Classification Search
CPC . A61M 1/16; A61P 25/00; A61P 25/14; A61P 7/08; B01D 2325/02; B01D 2325/04; B01D 2325/20; B01D 61/243; B01D 63/02; B01D 69/02; B01D 69/081; B01D 69/084; B01D 71/68
See application file for complete search history.

(56) References Cited

U.S. PATENT DOCUMENTS 7,875,183 B2    1/2011  Bradwell
2007/0203182 A1*  8/2007  Besana .................. A61P 25/00
                                                            514/317
(Continued)

FOREIGN PATENT DOCUMENTS

EP    2161072 A1    3/2010
EP    2253367 A1    11/2010
(Continued)

OTHER PUBLICATIONS

Ohayon et al.:Epidemiology of Restless Legs Syndrome: A Synthesis of the Literature. Sleep Med. Rev.16 (4), 2012: 283-95.
(Continued)

*Primary Examiner* — Kai H Weng
(74) *Attorney, Agent, or Firm* — Barnes & Thornburg LLP

(57) ABSTRACT

The present disclosure relates to a hemodialysis membrane for the treatment of restless leg syndrome (RLS), especially in severe and very severe cases and/or in patients which suffer from kidney failure and already receive hemodialysis. The present disclosure therefore also relates to methods of treating restless leg syndrome. The treatment and method encompasses using a hemodialysis membrane which is characterized in that it comprises at least one hydrophobic polymer and at least one hydrophilic polymer and in that it has a MWRO of between 8.5 and 14.0 kD and a MWCO of between 55 kD and 130 kD.

20 Claims, 3 Drawing Sheets

(51) Int. Cl.
    *A61K 31/197*     (2006.01)
    *A61K 31/381*     (2006.01)
    *A61K 31/404*     (2006.01)
    *B01D 61/24*     (2006.01)
    *B01D 69/02*     (2006.01)
    *B01D 69/08*     (2006.01)
    *B01D 71/68*     (2006.01)

(52) U.S. Cl.
    CPC ............ *A61K 31/404* (2013.01); *A61P 25/00* (2018.01); *B01D 61/243* (2013.01); *B01D 69/02* (2013.01); *B01D 69/084* (2013.01); *B01D 71/68* (2013.01); *B01D 2325/02* (2013.01); *B01D 2325/04* (2013.01); *B01D 2325/20* (2013.01)

(56) References Cited

U.S. PATENT DOCUMENTS

| | | | |
|---|---|---|---|
| 2012/0305487 | A1 | 12/2012 | Beck |
| 2015/0366907 | A1* | 12/2015 | Gupta .................... A61P 17/00 424/604 |
| 2017/0165615 | A1* | 6/2017 | Hornung .............. B01D 63/021 |
| 2017/0165616 | A1 | 6/2017 | Boschetti-De-Fierro |
| 2018/0042960 | A1* | 2/2018 | Thomsen ................ A61P 25/14 |

FOREIGN PATENT DOCUMENTS

| | | |
|---|---|---|
| WO | 2004/056460 | 7/2004 |
| WO | 2015/118045 | 8/2015 |
| WO | 2015/118046 | 8/2015 |

OTHER PUBLICATIONS

Allen et al.:Restless legs syndrome/Willis-Ekbom disease diagnostic criteria: updated International Restless Legs Syndrome Study Group (IRLSSG) consensus criteria—history, rationale, description, and significance. Sleep Medicine 15 (8), 2014 :860-873.

Kohnen et al.: Rating of daytime and nighttime symptoms in RLS: validation of the RLS-6 scale of restless legs syndrome/Willis-Ekbom disease. Sleep Medicine 20, 2016: 116-122.

Sinclair et al.: "Interventions for chronic kidney disease-associated restless legs syndrome". International Journal of Evidence-Based Healthcare 16 (3), 2018:182-184.

Araujo et al.: Restless legs syndrome in end-stage renal disease: Clinical characteristics and associated comorbidities. Sleep Medicine 11 (8), 2010: 785-790.

Ricardo et al.: Association of Sleep Duration, Symptoms, and Disorders With Mortality in Adults With Chronic Kidney Disease. Kidney International Reports 2, 2017, 866-873.

Dauvilliers et al.: Rotigotine in Hemodialysis-Associated Restless Legs Syndrome: A Randomized Controlled Trial: Am J Kidney Dis. 68 (3), 2016: 434-443.

Ward: J Am Soc Nephrol 16, 2005: 2421-2430.

Boschetti-De-Fierro et al.: "Extended characterization of a new class of membranes for blood purification: The high cut-off membranes", Int J Artif Organs 36 (7), 2013: 455-463.

Axelsson et al.: Loss of size selectivity of the glomerular filtration barrier in rats following laparotomy and muscle trauma. American Journal of Physiology—Renal Physiology, 297, 2009: F577-F582.

TH-PO296, J Am Soc Nephrol 29, 2018: 190.

* cited by examiner

MEMBRANE AND DEVICE FOR TREATING RESTLESS LEG SYNDROME

TECHNICAL FIELD

The present disclosure relates to a hemodialysis membrane for the treatment of restless leg syndrome (RLS), especially in severe and very severe cases and/or in patients which suffer from kidney failure and already receive hemodialysis. The present disclosure therefore also relates to methods of treating restless leg syndrome. The treatment and method encompasses using a hemodialysis membrane which is characterized in that it comprises at least one hydrophobic polymer and at least one hydrophilic polymer and in that it has a MWRO of between 8.5 and 14.0 kD and a MWCO of between 55 kD and 130 kD.

DESCRIPTION OF THE RELATED ART

Restless legs syndrome (RLS), also called Willis-Ekbom Disease, causes unpleasant or uncomfortable sensations in the legs and an irresistible urge to move them. Symptoms commonly occur in the late afternoon or evening hours, and are often most severe at night when a person is resting. Since symptoms can increase and become more severe during the night, it may become difficult for persons concerned to fall asleep or return to sleep after waking up. Moving the legs or walking typically relieves the discomfort but the sensations often recur once the movement stops (Ohayon et al.: Epidemiology of Restless Legs Syndrome: A Synthesis of the Literature. *Sleep Med Rev.* 16 (4), 2012: 283-95). RLS is classified as a sleep disorder since the symptoms are triggered by resting and attempting to sleep, and as a movement disorder, since people are forced to move their legs in order to relieve symptoms. It is, however, best characterized as a neurological sensorimotor disease, but the pathophysiological pathways are still unknown. The symptoms vary considerably in frequency from less than once a month or year to daily, and severity from mildly annoying to disabling. RLS is one of several disorders that can cause severe exhaustion and daytime sleepiness. As such, it can strongly affect mood, concentration, memory and general quality of life and health. Patients suffering from RLS are often unable to concentrate, have impaired memory, or fail to accomplish daily tasks. Untreated moderate to severe RLS can lead to about a 20 percent decrease in general productivity and can significantly contribute to depression and anxiety. More than 80 percent of people with RLS also experience periodic limb movement of sleep (PLMS). PLMS is characterized by involuntary leg (and sometimes arm) twitching or jerking movements during sleep that typically occur every 15 to 40 seconds, sometimes throughout the night. Although many individuals with RLS also develop PLMS, most people with PLMS do not experience RLS.

RLS/WED is diagnosed by ascertaining symptom patterns that meet the following five essential criteria, adding clinical specifiers where appropriate (Allen et al.: Restless legs syndrome/Willis-Ekbom disease diagnostic criteria: updated International Restless Legs Syndrome Study Group (IRLSSG) consensus criteria—history, rationale, description, and significance. *Sleep Medicine* 15 (8), 2014 :860-873). Essential diagnostic criteria (all must be met) are:

1. An urge to move the legs, usually but not always accompanied by, or felt to be caused by, uncomfortable and unpleasant sensations in the legs.
2. The urge to move the legs and any accompanying unpleasant sensations begin or worsen during periods of rest or inactivity such as lying down or sitting.
3. The urge to move the legs and any accompanying unpleasant sensations are partially or totally relieved by movement, such as walking or stretching, at least as long as the activity continues.
4. The urge to move the legs and any accompanying unpleasant sensations during rest or inactivity only occur or are worse in the evening or night than during the day.
5. The occurrence of the above features is not solely accounted for as symptoms primary to another medical or a behavioral condition (e.g. myalgia, venous stasis, leg edema, arthritis, leg cramps, positional discomfort, habitual foot tapping).

Specifiers for Clinical Course of RLS/WED:

A. Chronic-persistent RLS/WED: symptoms when not treated would occur on average at least twice weekly for the past year.

B. Intermittent RLS/WED: symptoms when not treated would occur on average <2/week for the past year, with at least five lifetime events.

The severity of RLS can be rated as mild, moderate, severe or very severe according to the International Restless Legs Syndrome Study Group (IRLS) Rating Scale, even though other methods, such as the RLS-6 scale (Kohnen et al.: Rating of daytime and nighttime symptoms in RLS: validation of the RLS-6 scale of restless legs syndrome/ Willis-Ekbom disease. *Sleep Medicine* 20, 2016: 116-122) are available as well. The IRLS is the most widely used of the scales rating the severity of RLS/WED. It has been well validated and is the primary end point for most therapeutic and nontherapeutic studies of RLS/WED. It is based on psychometric properties. An IRLS score of 11-20 relates to moderate, 21-30 to severe and 31-40 to very severe RLS. The general well-being and quality of life of dialysis patients can also be assessed with the KDQOL™-36 survey (Kidney Disease and Quality of Life™ (KDQOL™-36), Copyright© 2000 by RAND and the University of Arizona), in which patients will be asked to answer question on general health, how the patients feel and their background. The KDQOL™-36 helps to evaluate how a patient feels about his or her care and provide further understanding about the effects of medical care on the health of patients.

The estimated prevalence of the RLS, for example, is around 7-10% in Caucasians (Ohayon et al., *Sleep Med Rev.* 16 (4), 2012: 283-95). RLS occurs in both men and women, although women are more likely to have it than men. It may begin at any age. Many individuals who are severely affected are middle-aged or older, and the symptoms typically become more frequent and last longer with age. The pathophysiology of RLS remains unclear, even though there is some mounting evidence that points to dopaminergic and brain-iron dysregulation together with a genetic component. The cause of RLS is otherwise classified as primary or secondary (Sinclair et al.: "Interventions for chronic kidney disease-associated restless legs syndrome". *International Journal of Evidence-Based Healthcare* 16 (3), 2018:182-184). Primary RLS is idiopathic with no known cause but seems to be linked to genetic risk factors. Secondary RLS is associated with certain clinical conditions such as peripheral neuropathy, iron deficiency, type 2 diabetes, Parkinson's disease and multiple sclerosis.

About 12% to 25% of patients with end-stage renal disease (ESRD) are affected by RLS as well (Araujo et al.: Restless legs syndrome in end-stage renal disease: Clinical characteristics and associated comorbidities. *Sleep Medicine*

11 (8), 2010: 785-790 and Ricardo et al.: Association of Sleep Duration, Symptoms, and Disorders With Mortality in Adults With Chronic Kidney Disease. *Kidney International Reports* 2, 2017, 866-873).

Current medication approaches for RLS, in general, depend on the individual and the suspected reason for RLS, but may include supplementation with iron; alpha 2 agonists, specifically in cases of primary RLS; ibuprofen, a non-steroidal anti-inflammatory drug (NSAID), in case of mild symptoms; anticonvulsants, such as neurontin, or gabapentin; benzodiazepines in case of persistent and mild symptoms, including, for example, Restoril or temazepam, Xanax or alprazolam, and Klonopin or clonazepam; dopaminergic agents which raise the levels of dopamine, a neurotransmitter, in the brain, thereby addressing the unpleasant leg sensations associated with RLS, for example Levodopa and carbidopa; and opiates which may be used when other medications have failed, such as codeine and propoxyphene (low dose opiates), oxycodone hydrochloride, methadone hydrochloride, and levorphanol tartrate (high-dose opiates).

Dopamine agonists, such as ropinirole and levodopa, which also raise brain dopamine levels and treat unpleasant leg sensations but which may cause adverse effects especially in older patients. In addition, the effectiveness of these treatments has not been established in patients with chronic kidney disease (Sinclair et al., 2018). Rotigotine was used, with some success, in hemodialysis-associated restless legs syndrome (Dauvilliers et al.: Rotigotine in Hemodialysis-Associated Restless Legs Syndrome: A Randomized Controlled Trial: Am J Kidney Dis. 68 (3), 2016: 434-443).

Consequently, new approaches to act on RLS, specifically in severe or very severe cases, would be highly desirable.

Appropriate hemodialysis, especially, but not only, in end stage renal disease patients who are already receiving hemodialysis treatment, for treating or ameliorating RLS, would be a useful and immediate possibility to address RLS. However, this would require a hemodialysis filter or dialyzer which could significantly ameliorate RLS. No such dialyzer is currently described or known which would ameliorate RLS in patients concerned. In contrast, end stage renal disease patients on hemodialysis are often especially concerned by RLS. It is not understood how the hemodialysis and the respective hemodialyzers used in that therapy influence the emergence or persistence of RLS or how they can contribute to ameliorating RLS in a patient. However, it would significantly contribute to especially hemodialysis patients' quality of life if the occurrence of RLS could be reduced or avoided through using an appropriate dialyzer. Especially in severe or very severe cases of RLS according to the IRLS score, where medication does not show any significant effect or is accompanied by intolerable side effects, regular or intermittent hemodialysis could be an option also in non-renal patients suffering from another secondary RLS, such as, for example, multiple sclerosis or Parkinson's disease, or from primary RLS.

In general, dialysis membranes are designed to accomplish the removal of uremic toxins and excess water from the blood of patients with chronic renal failure while balancing the electrolyte content in the blood with the dialysis fluid. The sieving property of a membrane, i.e., its permeability to solutes, is determined by the pore size and sets the maximum size for the solutes that can be dragged through the membrane with the fluid flow. The sieving coefficient for a given substance could be simply described as the ratio between the substance concentration in the filtrate and its concentration in the feed (i.e., the blood or plasma), and is therefore a value between 0 and 1. Assuming that the size of a solute is proportional to its molecular weight, a common way to illustrate the properties of membranes is by creating a sieving curve, which depicts the sieving coefficient as a function of the molecular weight. The molecular weight cut-off (MWCO) is defined as the molecular weight where the sieving coefficient is 0.1 (FIG. 1). The sieving curve determined for a polydisperse dextran mixture can be considered a standard characterization technique for a membrane. Conventional dialysis membranes are classified as low-flux or high-flux, depending on their permeability. A third group, called protein leaking membranes, is also available on some markets. These three membrane groups were described in a review by Ward (2005), J Am Soc Nephrol 16: 2421-2430. A fourth type which has emerged some time ago is the above-mentioned high cut-off or HCO membranes, which have very particular characteristics (Boschetti-de-Fierro et al. (2013): "Extended characterization of a new class of membranes for blood purification: The high cut-off membranes", *Int J Artif Organs* 36(7), 455-463). A concise summary of the general classification and performance of said membranes is shown in Boschetti-de-Fierro et al., and the respective expressions for such membranes and/or dialyzers ("low flux" or "high flux" (HF), "high cut-off (HCO)" and "protein leaking") are used herein in accordance with the definition given in Boschetti-de-Fierro et al (2013). The latest step in membrane development is a membrane type which is positioned in the gap between the high flux and high cut-off membranes. Said membranes are also referred to as "medium cut-off" membranes (see also Table I). These membranes and how they can be prepared are described in detail in PCT/EP2015/052365. Hemodialyzers based on such membranes are described in detail in PCT/EP2015/052364. Theranova® (Baxter) is an example for a dialyzer which is meanwhile commercially available and which fulfills the criteria for a medium cut-off dialyzer in terms of MWRO and MWCO as further defined herein.

The most evident difference among the types of membranes mentioned above is their position along the molecular weight axis (FIG. 2). High-flux membranes have a sieving curve which reflects their ability to remove toxins of small molecular weight such as urea. They also allow the removal of relatively large toxins, such as 132-microglobulin and myoglobin. High cut-off membranes show a sieving curve located at higher molecular weights than that for the glomerular membrane. Although the high cut-off sieving profile resembles that of the glomerular membrane up to 20 kDa, the high cut-off membranes are open toward molecular weights higher than 20 kDa. This means that the high cut-off membranes allow some passage of proteins which would be retained by the glomerular membrane. WO 2004/056460 already discloses certain early high cut-off membranes. An advanced dialyzer with a high cut-off membrane which is currently on the market is, for example, Theralite® (Baxter). Known uses of high cut-off membranes include treatment of chronic inflammation (EP 2 161 072 A1), amyloidosis and rhabdomyolysis and treatment of anemia (US 2012/0305487 A1), the most explored therapy to date being the treatment of myeloma kidney (U.S. Pat. No. 7,875,183 B2). In this case, the removal of the free light chains in patients with multiple myeloma on chemotherapy has allowed the recovery of kidney function in a significant number of patients. As is shown in Table I, such high cut-off membranes are characterized by a molecular retention onset (MWRO) of between 15.0 kDa and 20.0 kDa and a molecular weight cut-off (MWCO) of between 170 kDa and 320 kDa as determined by dextran sieving curves before the membrane has had contact with blood or a blood product. Due to the loss of up to 40 g of albumin per session with the above-mentioned dialyzers, high cut-off membranes will mainly be used for acute applications, although some physicians have contemplated benefits of using them in chronic applications, possibly in conjunction with albumin substitution.

The development of the before mentioned medium cut-off membranes and dialyzers filled the gap between high-flux and high cut-off dialyzers. Such semipermeable membranes are characterized by a molecular retention onset (MWRO) of between 9.0 kDa and 14.0 kDa and a molecular weight cut-off (MWCO) of between 55 kDa and 130 kDa as determined by dextran sieving curves before the membrane has had contact with blood or a blood product. Due to this very unique sieving profile the membranes considerably extend the performance of current high-flux membranes and dialyzers, as they allow for the removal of middle and large uremic solutes which cannot be addressed by the current high-flux membranes. They are, therefore, also referred to as "membranes with increased permeability" and hemodialysis with Theranova® as expanded hemodialysis therapy (HDx). At the same time, such membranes are able to remove higher molecular weight compounds without having to face unacceptable albumin losses during treatment. Consequently, these membrane types can be used in both acute and chronic settings. For the avoidance of doubt, the expression "membrane(s) with increased (or "extended") permeability" as used herein is equivalent with the expression "medium cut-off membrane".

The expression "molecular weight cut-off" or "MWCO" or "nominal molecular weight cut-off" as used herein is a value for describing the retention capabilities of a membrane and refers to the molecular mass of a solute where the membranes have a rejection of 90% (see above and FIG. 1), corresponding to a sieving coefficient of 0.1. The MWCO can alternatively be described as the molecular mass of a solute, such as, for example, dextrans or proteins where the membranes allow passage of 10% of the molecules. The shape of the curve depends, to a considerable degree, on the pore size distribution and is thus linked to the physical appearance of the membrane. As already mentioned, sieving curves give relevant information in two dimensions: the shape of the curve describes the pore size distribution, while its position on the molecular weight axis indicates the size of the pores. Molecular weight cut-off (MWCO) limits the analysis of the sieving curve to only one dimension, namely to the size of the pores where the sieving coefficient is 0.1. To enhance membrane characterization the molecular weight retention onset (MWRO) has been introduced for characterizing membranes such as high cut-off and medium cut-off membranes (Boschetti-de-Fierro et al.). The MWRO is defined as the molecular weight at which the sieving coefficient is 0.9, as schematically shown in FIG. 1. It is analogous to the MWCO and describes when the sieving coefficient starts to fall from 1 to 0, i.e. when the membrane starts to reject compounds of a certain size. Defining two points on the sieving curves allows a better characterization of the sigmoid curve, giving an indication of the pore sizes and also of the pore size distribution. The expression "molecular weight rejection onset" or "MWRO" or "nominal molecular weight rejection onset", as used herein, therefore refers to the molecular mass of a solute where the membranes have a rejection of 10%, or, in other words, allow passage of 90% of the solute, corresponding to a sieving coefficient of 0.9.

TABLE I

General classification of hemodialysis membranes based on dextran sieving

| Dialyzer Type | Structural Characteristics | | |
|---|---|---|---|
| | MWRO [kDa] | MWCO [kDa] | Pore radius [nm] |
| Low-flux | 2-4 | 10-20 | 2-3 |
| High-flux | 5-10 | 25-65 | 3.5-5.5 |
| Protein leaking | 2-4 | 60-70 | 5-6 |
| High cut-off | 15-20 | 170-320 | 8-12 |
| Medium cut-off | 9.0-14.0 | 55-130 | 5.5 < pore radius < 8.0 |

The applicants have found that medium cut-off membranes as defined above and in Table I can be used to effectively address RLS in a patient. The extended permeability of the medium cut-off membranes has a surprising effect on RLS also in hemodialysis patients. More specifically, the inventors were able to show a reduction of RLS by treatments with the membranes with increased permeability, thereby demonstrating that dialyzers comprising medium cut-off membranes are an effective method to treat or ameliorate the symptoms of RLS.

SUMMARY OF THE INVENTION

It was the object of the present invention to provide for a method of treating or ameliorating restless leg syndrome (RLS) in a patient diagnosed with RLS, the method comprising withdrawing and bypassing the blood of the patient in a continuous flow into contact with one face of the membrane, simultaneously passing dialysate solution in a continuous flow on the opposite face of the membrane, and returning the blood to the patient, wherein the hemodialysis membrane is characterized in that it comprises at least one hydrophobic polymer and at least one hydrophilic polymer and in that it has a MWRO of 8.5 kD and 14.0 kD and a MWCO of between 55 kD and 130 kD. The MWRO and MWCO values for a given membrane are based on dextran sieving experiments before blood contact of the membrane as described by Boschetti-de-Fierro et al., 2013, and in PCT/EP2015/052364. The present disclosure therefore relates to medium cut-off membranes for the treatment of patients suffering from restless leg syndrome (RLS). The hemodialysis treatment with medium cut-off membranes is preferably applied in cases where RLS is classified as severe or very severe, where medication is contraindicated or does not result in an improvement of the condition, and where patients are already undergoing hemodialysis treatment. The medium cut-off membrane based hemodialysis treatment of patients concerned can preferably be combined with a medication comprising dopamine agonists.

DETAILED DESCRIPTION

Figure 1:
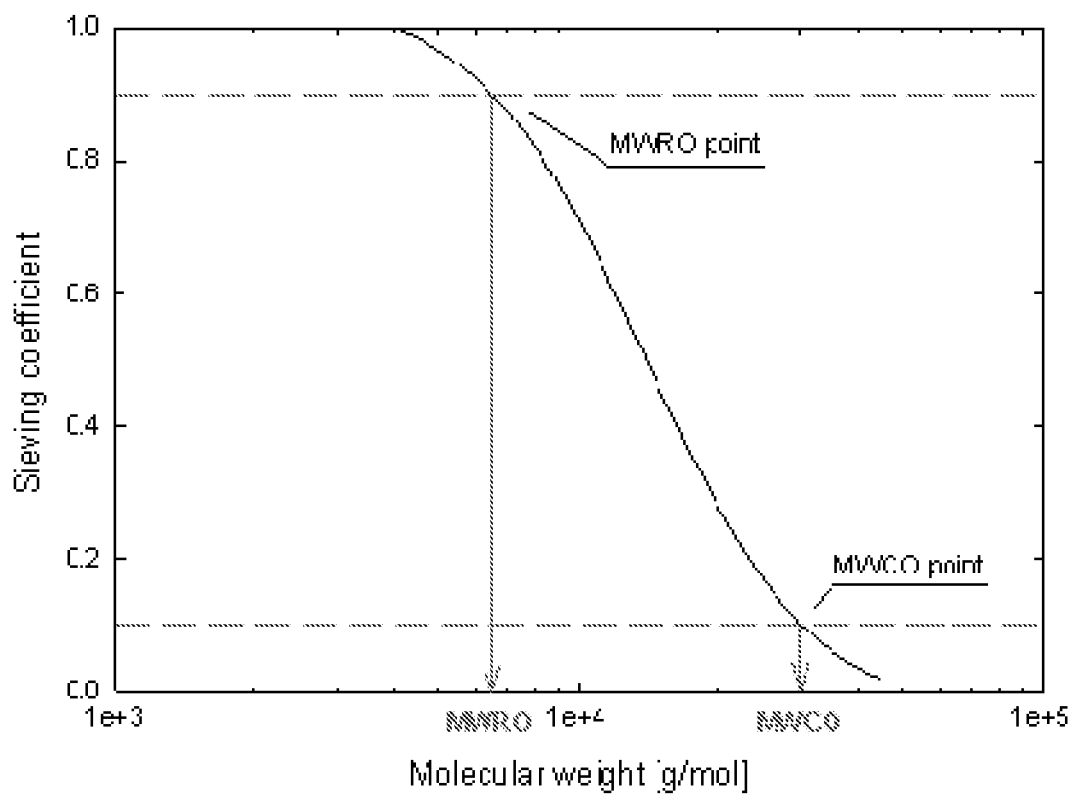
FIG. 1 is a representation of a dextran sieving curve where the values of molecular weight retention onset (MWRO, achieved at SC=0.9) and molecular weight cut-off (MWCO, achieved at SC=0.1) are illustrated.
Figure 2:
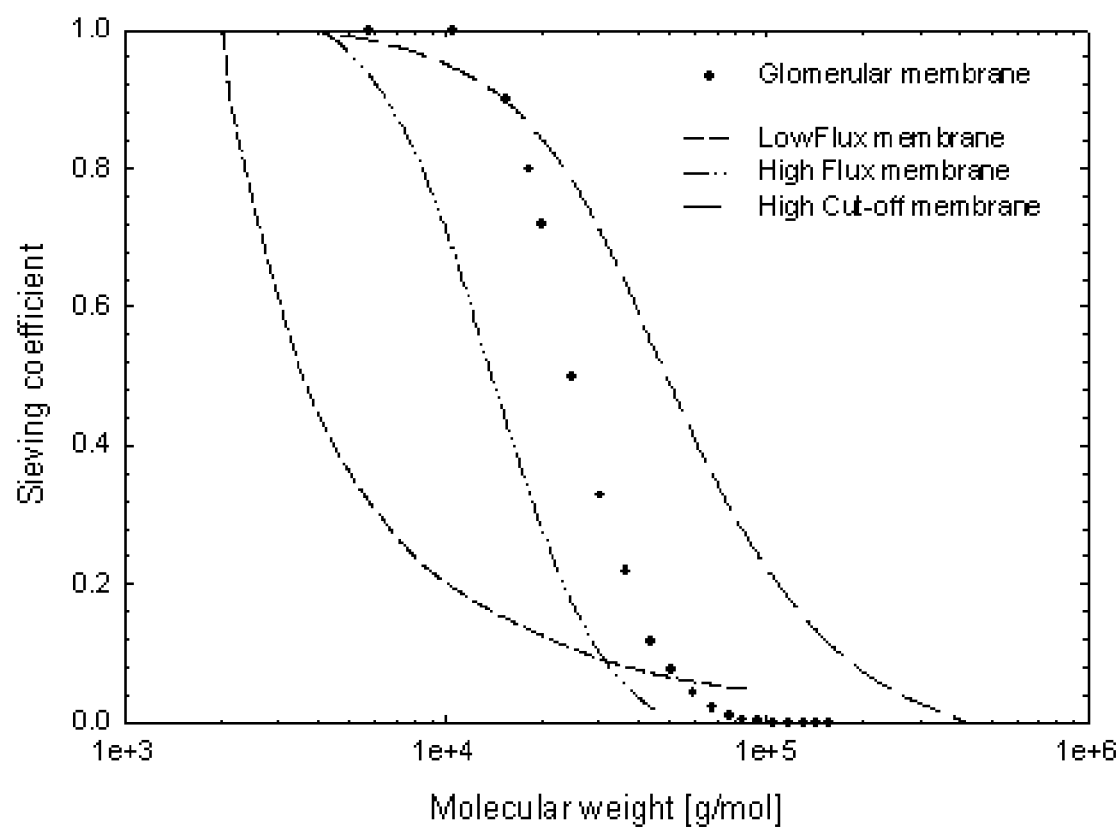
FIG. 2 shows characteristic dextran sieving curves for the different types of dialysis membranes: low flux, high flux and high cut-off. The data for the glomerular membrane (as reported by Axelsson et al. (2009): Loss of size selectivity of the glomerular filtration barrier in rats following laparotomy and muscle trauma. American *Journal of Physiology—Renal Physiology,* 297, F577-F582) has been added for illustration.
Figure 3:
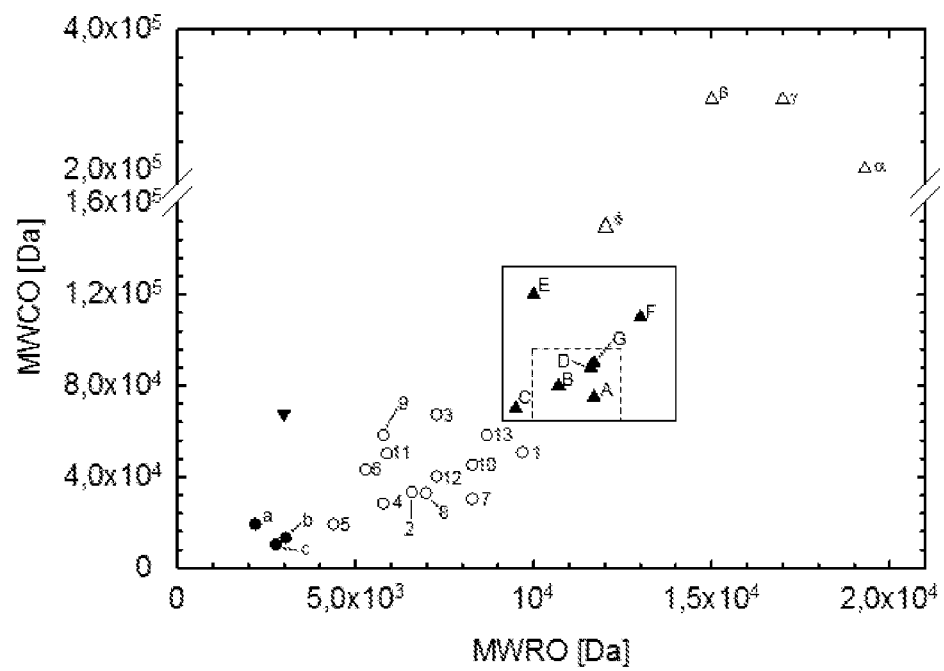
FIG. 3 shows a mapping of different types of blood membranes based on the molecular weight retention onset and molecular weight cut-off from dextran sieving curves. The dotted line squares approximately represent the boundaries that delimit the dialyzer families. The letters and numbers denote various membranes as further defined in US 2017/165616 A1.

Restless leg syndrome (RLS), also referred to as Willis-Ekbom disease (WED), is well known neurological, sensimotor disorder, which is generally characterized by a nearly irresistible urge to move the legs. Restless leg syndrome may be classed as mild, severe or very severe, depending on the frequency and severity of the symptoms, how well the symptoms can be relieved by moving around, and how much disturbance they cause.

The expression "restless leg syndrome" or "RLS" as used herein refers to the condition fulfilling the diagnostic criteria of the International Restless Legs Syndrome Study Group (IRLSSG) developed updated diagnostic criteria for restless legs syndrome/Willis-Ekbom disease (RLS/WED), see Allen et al.: Restless legs syndrome/Willis-Ekbom disease diagnostic criteria: updated International Restless Legs Syndrome Study Group (IRLSSG) consensus criteria—history, rationale, description, and significance. *Sleep Medicine* 15 (8), 2014, 860-873.

The following numbered embodiments are contemplated and are non-limiting:

1. A hollow-fiber membrane having a MWRO of between about 8.5 kD and about 14.0 kD and a MWCO of between about 55 kD and about 130 kD as determined by dextran sieving before blood contact of the membrane,
   wherein the hollow-fiber membrane comprises at least one polymer selected from the group consisting of polysulfone, polyethersulfone and polyarylethersulfone, and
   wherein the hollow-fiber membrane further comprises polyvinylpyrrolidone, for use in a method of treating or ameliorating restless leg syndrome (RLS) in a patient diagnosed with RLS, the method comprising withdrawing and bypassing the blood of the patient in a continuous flow into contact with one face of the membrane, simultaneously passing dialysate solution in a continuous flow on the opposite face of the membrane, and returning the blood to the patient.

2. A hollow-fiber membrane for a use according to clause 1, wherein the membrane has a MWRO of between about 9.0 kD and about 14.0 kD and a MWCO of between about 55 kD and about 110 kD as determined by dextran sieving before blood contact of the membrane.

3. A hollow-fiber membrane for a use according to clause 1 or clause 2 wherein the patient fulfills the International Restless Legs Syndrome Study Group (IRLSSG) consensus criteria.

4. A hollow-fiber membrane for a use according to any of clauses 1 to 3, wherein the patient has a IRLS score of 11-20 (moderate), 21-30 (severe) or 31-40 (very severe).

5. A hollow-fiber membrane for use according to any of clauses 1 to 4, wherein the patient receives concomitant medication with dopamine agonists, such as, for example, Rotigotine.

6. A hollow-fiber membrane for a use according to any of clauses 1 to 5, wherein the patient is a hemodialysis patient.

7. A hollow-fiber membrane for a use according to any of clauses 1 to 6, wherein the average effective pore size (radius) on the selective layer of the membrane as derived from the MWCO based on dextran sieving is above about 5.0 nm and below about 7.0 nm.

8. A hollow-fiber membrane for a use according to any of clauses 1 to 7, wherein the inner diameter of the membrane is below about 200 μm and the wall thickness is below about 40 μm.

9. A method of treating restless leg syndrome (RLS) in a patient, comprising withdrawing and bypassing the blood of the patient in a continuous flow into contact with one face of a membrane, simultaneously passing dialysate solution in a continuous flow on the opposite face of the membrane, and returning the blood to the patient, wherein the membrane has a MWRO of between about 8.5 kD and about 14.0 kD and a MWCO of between about 55 kD and about 130 kD as determined by dextran sieving before blood contact of the membrane, and wherein the membrane comprises at least one polymer selected from the group of polymers consisting of polysulfone, polyethersulfone and polyarylethersulfone, and further comprising polyvinylpyrrolidone.

10. A method of treating restless leg syndrome (RLS) according to clause 9, wherein the hollow fiber membrane is characterized in that it has a MWRO of between about 9.0 kD and about 14.0 kD and a MWCO of between about 55 kD and about 110 kD as determined by dextran sieving before blood contact of the membrane.

11. A method of treating restless leg syndrome (RLS) according to clause 9 or 10, wherein the patient fulfills the International Restless Legs Syndrome Study Group (IRLSSG) consensus criteria.

12. A method of treating restless leg syndrome (RLS) according to any of clauses 6 to 11, wherein the patient has a IRLS score of 11-20 (moderate), 21-30 (severe) or 31-40 (very severe).

13. A method of treating restless leg syndrome (RLS) according to any of clauses 9 to 12, wherein the patient receives concomitant medication with dopamine agonists.

14. A method of treating restless leg syndrome (RLS) according to any of clauses 9 to 13, wherein the patient is a hemodialysis patient.

15. A method of treating restless leg syndrome (RLS) according to any of clauses 9 to 14, wherein the average effective pore size (radius) on the selective layer of the membrane as derived from the MWCO based on dextran sieving is above about 5.0 nm and below about 7.0 nm.

16. A method of treating restless leg syndrome (RLS) according to any of clauses 9 to clause 15, wherein the inner diameter of the membrane is below about 200 μm and the wall thickness is below about 40 μm.

17. A method of treating restless leg syndrome (RLS) according to any of clauses 9 to 16, wherein the membrane is comprised in a fiber bundle which has a packing density of from about 53% to about 60% and wherein the fiber bundle comprises at least 80% crimped fibers.

18. A method of treating restless leg syndrome (RLS) according to any of clauses 9 to 16, wherein the membrane is comprised in a fiber bundle which has a packing density of from about 53% to about 60% and wherein the fiber bundle consists of at least 80% crimped fibers.

The present disclosure relates to medium cut-off membranes for extended hemodialysis for the treatment of patients suffering from restless leg syndrome (RLS). The hemodialysis treatment is preferably applied in cases where RLS is classified as severe or very severe, both in primary or secondary RLS. The treatment is further recommended where medication is contraindicated or does not result in an improvement of the condition. It is also specifically suited where patients are already undergoing hemodialysis treatment. The treatment is especially indicated in cases where a hemodialysis patient suffers from a severe or very severe RLS and wherein medication does not result in an improvement of the RLS symptoms. The treatment is, however, also recommended in conjunction with the administration of dopamine agonists, such as, for example, ropinirole or levodopa, and especially with rotigotine.

The method of treating a patient suffering from RLS comprises withdrawing and bypassing the blood from the patient in a continuous flow into contact with one face of an hemodialysis membrane, simultaneously passing dialysate solution in a continuous flow on an opposite face of the hemodialysis membrane to the side of the hemodialysis membrane in contact with the blood, the flow of the dialysate solution being counter-current to the direction of flow of blood, and returning the blood to the patient, wherein the hemodialysis membrane is characterized in that it has a MWRO of between 8.5 kDa and 14 kDa and a MWCO of between 55 kDa and 130 kDa.

According to a specific embodiment of the invention, the hemodialysis membrane for treatment of RLS is characterized in that it is prepared from a polymer blend of polysulfone or polyethersulfone and polyvinylpyrrolidone and in that it has a MWRO of 9 kDa and 12.0 kDa and a MWCO of between 55 kDa and 110 kDa. According to another embodiment of the invention, it is prepared from a polymer blend of polysulfone or polyethersulfone and polyvinylpyrrolidone and in that it has a MWRO of 9 kDa and 12.0 kDa and a MWCO of between 55 kDa and 90 kDa. The MWRO and MWCO values as used herein for a given membrane are based on dextran sieving experiments as described by Boschetti-de-Fierro et al. (2013,) see "Materials and Methods" section of the reference, and refer to values obtained before blood contact of the membrane.

According to a specific embodiment of the present invention, the treatment continuous treatment of (anticipated) moderate to severe hemolysis, RLS in a patient can be treated with a hemodialysis membrane according to the invention in the form of a continuous renal replacement therapy (CRRT) or during standard (chronic) hemodialysis treatment which is administered to patients suffering from end-stage renal disease. Such membranes, in the context of the present invention, are referred to as "medium cut-off membranes" or, alternatively, as "membranes having extended permeability". As mentioned before, these membranes are described in detail in PCT/EP2015/052365. The said membranes and dialyzers comprising same, in comparison to membranes and dialyzers known from the prior art, are characterized by their ability to effectively reduce RLS symptoms as evidenced in the COREXH study, see Example Section of this application. They can be used safely over a prolonged treatment time according to the invention, either in addition to one of the medication treatments mentioned above.

According to a specific embodiment of the invention, the above described membranes with extended permeability and hemofilters based thereon can also be used as stand-alone filters for hemodialysis treatments. In addition to performing a normal hemodialysis treatment on patients suffering from renal disease and showing RLS symptoms according to the invention, and wherein RLS is treated concomitantly, the said membranes and filters can also be used for treating patients suffering from RLS, especially from severe or very severe forms, for example for regular treatments once, twice or three times a week for up to four hours, or intermittently, during acute episodes of severe or very severe RLS and with or without concomitant medication, e.g. with dopamine antagonists. Such intermittent treatment can be performed, for example, as a standard hemodialysis treatment for two to five hours, or in the form of CRRT for a prolonged period of time.

Accordingly, the membrane for treating RLS according to the invention is prepared from a polymer blend of polysulfone, polyethersulfone or polyarylethersulfone and polyvinylpyrrolidone and has a MWRO of between 8.5 kDa and 14.0 kDa and a MWCO of between 55 kDa and 130 kDa. According to a specific embodiment of the invention, the membrane is used for treating RLS in end stage renal disease patients. According to another embodiment of the invention, the membrane with extended permeability has a MWRO in the range of from 9.0 kDa to 12.5 kDa and a MWCO in the range of from 55 kDa to 110 kDa. According to another aspect of the present invention, said membrane has a MWRO in the range of from 9.0 kDa to 12.5 kDa and a MWCO in the range of from 68 kDa to 110 kDa. According to yet another aspect of the present invention, said membrane has a MWRO in the range of from 9 kDa to 12.5 kDa and a MWCO in the range of from 55 kDa to 90 kDa. According to yet another aspect of the present invention, said membrane has a MWRO of more than 8.5 kDa and less than 12.5 kDa and a MWCO of more than 55.0 kDa and less than 90.0 kDa. According to yet another aspect of the present invention, a membrane and dialyzer as commercially available under the tradename Theranova® is used for the treatment of RLS according to the invention.

It was found in a clinical study on the effects of using medium cut-off membranes and dialyzers comprising same, that a hemodialysis treatment according to the invention leads to a significant reduction of RLS symptoms.

The medium cut-off membranes can be processed into hemodialysis filters by methods generally known in the art, for example, into hemodialysis filters having a design in terms of housing, area, fiber and bundle geometry, packing density and flow characteristics, similar to or the same as products already available on the market such as, for example, Theranova®, or as described for medium cut-off membranes in PCT/EP2015/052364, which is herein incorporated by reference in its entirety. Accordingly, the use of the expression "medium cut-off membrane" in the context of the present invention encompasses the use of the membrane within an adequate filter device fit for being used in/on an extracorporeal dialysis machine.

According to one aspect of the invention, the hemodialysis treatment with said medium cut-off membranes according to the invention is performed from 2 to 4 times per week for a period of from 2 to 6 hours, respectively, and thus is not different from a standard hemodialysis treatment. According to another aspect of the present invention a treatment may continue until RLS symptoms have decreased to acceptable values or completely disappeared. Depending on the specific condition of a patient, such treatment regimens or routines as described above can be applied singularly or regularly.

According to one embodiment of the invention, the hemodialysis treatment according to the invention can be supplemented by a state of the art medication which would otherwise be prescribed to a patient suffering from a disease which is causally connected to RLS.

Dialysis machines which can be used for performing a treatment according to the invention are standard dialysis machines. Examples for such devices are the AK 96, AK 200 S and AK 200 ULTRA S, PrismafleX eXeed or the Artis dialysis machines of Baxter. However, any other dialysis machine can also be used for the treatment.

Parameters for performing a treatment according to the invention can be adjusted to standard dialysis treatment or medium cut-off parameters and the specifications of the medium cut-off membrane. Typical flow rates used for the present treatment may vary. It is advantageous to use flow rates with a QB (blood flow) of 100-500, preferably 250-400 ml/min and a QD (dialysate flow rate) of 100-1000, preferably 300-500 ml/min.

An improvement of the patient's conditions can be reviewed, for example, by determining the severity of RLS with the help of the IRLS scale.

According to one aspect of the present invention, the dialysis membrane according to the invention comprises at least one hydrophilic polymer and at least one hydrophobic polymer. In one embodiment, at least one hydrophilic polymer and at least one hydrophobic polymer are present in the dialysis membrane as domains on the surface of the dialysis membrane. The hydrophobic polymer may be chosen from the group consisting of polyarylethersulfone (PAES), polypropylene (PP), polysulfone (PSU), polymethylmethacrylate (PMMA), polycarbonate (PC), polyacrylonitrile (PAN), polyamide (PA), polytetrafluorethylene (PTFE) or combinations thereof. In one embodiment of the invention, the hydrophobic polymer is chosen from the group consisting of polyarylethersulfone (PAES), polypropylene (PP), polysulfone (PSU), polycarbonate (PC), polyacrylonitrile (PAN), polyamide (PA) polytetrafluorethylene (PTFE) or combinations thereof. In another embodiment of the invention, the hydrophobic polymer is chosen from the group consisting of polyarylethersulfone (PAES), polyethersulfone (PES) and polysulfone (PSU). The hydrophilic polymer may be chosen from the group consisting of polyvinylpyrrolidone (PVP), polyethyleneglycol (PEG), polyvinylalcohol (PVA), and copolymer of polypropyleneoxide and polyethyleneoxide (PPO-PEO). In one embodiment of the invention, the hydrophilic polymer may be chosen from the group consisting of polyvinylpyrrolidone (PVP), polyethyleneglycol (PEG) and polyvinylalcohol (PVA). In one embodiment of the invention, the hydrophilic polymer is polyvinylpyrrolidone (PVP).

Membranes with extended permeability (or medium cut-off membranes) are disclosed and can be prepared as described in PCT/EP2015/052364, which is herein incorporated by reference in its entirety. Comparable membranes which can also effectively be used according to the invention and methods for preparing them are described in EP 2 253 367 A1, which is herein incorporated by reference in its entirety.

In conclusion, the findings of the inventors in this case demonstrate the possibility of treating RLS according to the invention by using extracorporeal blood purification techniques based on medium cut-off dialyzers according to the invention. For example, the combination of a Theranova® filter with the AK96 dialysis machine for the treatment of RLS in combination with standard hemodialysis treatment in an ESRD patient demonstrates a significant clinical benefit in this study and might represent a suitable choice for efficient RLS treatment in an acute setting and for the treatment of severe RLS episodes.

It will be readily apparent to one skilled in the art that various substitutions and modifications may be made to the invention disclosed herein without departing from the scope and spirit of the invention. The present invention will be illustrated by way of non-limiting examples in the Examples section in order to further facilitate the understanding of the invention.

EXAMPLES

Example 1

Clinical outcomes for RLS in patients on treatment with expanded hemodialysis (HDx), based on a registry of conventional clinical practice in Colombia (TH-P0296, *J Am Soc Nephrol* 29, 2018: 190)

1.1 Study Design

This study aimes at evaluating the effectiveness of expanded hemodialysis performed with medium cut-of dialyzers on, for example, RLS, based on actual data from a group of patients prevalent in chronic hemodialysis treatment, in the network of RTS renal clinics in Colombia. The study is a prospective cohort, multicenter, observational study. The study data will be captured from the first hemodialysis session after enrollment in the study and signing of the informed consent form. Each subject will participate in the study over a period of 1 year. The purpose of this study, among other aspects, was to evaluate changes in quality of life and prevalence of restless legs in the first six months after initiating a change in dialysis therapy from high-flux HD to HDx.

1.2 Study Population

Up to 1,000 subjects who receive expanded dialysis treatment with the Theranova® dialyzer (medium cut-off dialyzer) at least 3 times per week and with a minimum of 4 hours per session. Each subject must meet the following inclusion criteria in order to be enrolled in this study. The patients must be ≥18 years old and have been diagnosed with CKD with more than 90 days in chronic hemodialysis, undergoing a hemodialysis schedule at least 3 times per week and a minimum duration of 4 hours per session. The duration of hemodialysis treatment for each elected patient varies depending on their current expanded HD treatment prescription as determined by their treating physician.

1.3 Dialyzers

Patients were converted from high-flux HD to HDx with the Theranova dialyzer in 12 renal clinics of the Renal Therapy Services (RTS) Colombia network. The dialyzer used in the study was the following: Theranova® (Baxter International, Inc.).

1.4 Outcomes

Patient-reported outcome measures were the following:
(1) Individual item scores and total scores for DSI and KDQOL™-36 and frequency of restless legs diagnosis according to IRLS.
(2) Number of use of phosphorus chelating agents and plasma phosphorus level.
(3) Dose of erythropoietin and hemoglobin level.
(4) Number of antihypertensive drugs and systolic and diastolic blood pressure.
(5) Intake of tablets/pills per day and KDQOL™-36 Score.
(6) Use of nutritional supplements and nutritional status.

1.5 Concomitant Medication Assessment

The details of predefined concomitant drugs of interest, which were, for example, erythropoiesis stimulating agents (ESA), HD anticoagulants, phosphate binders, dopamine agonists, iron supplements and antihypertensives, given during the 30-day interval before the subject's enrollment in the study and during the year of follow-up, were captured.

1.6 Results 666 patients were evaluated, 61.4% (n=409) were men, the mean age was 59.8 years (SD=15.3), 60.3% were more than 3 years on hemodialysis. It was found that there were significant improvements in a large part of the dimensions in quality of life (see Table II), and a significant reduction of the diagnosis of restless legs (Table III).

TABLE II

KDQOLTM-36 Quality of Life

| KDQOLTM 36 | Baseline Mean (SD) | Six months Mean (SD) | Difference | P value* |
|---|---|---|---|---|
| Symptom/problem list | 77.75 (16.05) | 81.08 (15.07) | 3.30 | 0.0000 |
| Effects of kidney disease | 68.90 (22.31) | 72.70 (21.89) | 3.84 | 0.0000 |
| Burden of kidney disease | 46.48 (27.66) | 50.23 (29.74) | 3.72 | 0.0006 |
| SF-12 Physical Health Composite | 40.98 (11.24) | 41.13 (11.39) | 0.14 | 0.6670 |
| SF-12 Mental Health Composite | 51.05 (11.78) | 52.10 (11.15) | 1.01 | 0.0348 |

TABLE III

Diagnostic Criteria RLS (IRLS Score)

| Diagnostic Criteria of Restless Legs | Baseline N (%) | Six months N (%) | Difference % | P value** |
|---|---|---|---|---|
| Diagnostic Criteria of Restless Legs | 155 (23.34) | 76 (11.46) | 11.88 | 0.0000 |

*Anova
**McNemar Test

The invention claimed is:

1. A method of treating restless leg syndrome (RLS) in a patient, said method comprising the steps of withdrawing and bypassing the blood of the patient in a continuous flow into contact with one face of a membrane, simultaneously passing dialysate solution in a continuous flow on the opposite face of the membrane, and returning the blood to the patient,
   wherein the membrane has a MWRO of between about 8.5 kD and about 14.0 kD and a MWCO of between about 55 kD and about 130 kD as determined by dextran sieving before blood contact of the membrane, and
   wherein the membrane comprises at least one polymer selected from the group of polymers consisting of polysulfone, polyethersulfone and polyarylethersulfone, and further comprising polyvinylpyrrolidone,
   wherein treatment with the membrane reduces one or more RLS symptoms in the patient.

2. The method of treating restless leg syndrome (RLS) according to claim 1, wherein the hollow fiber membrane is characterized in that it has a MWRO of between about 9.0 kD and about 14.0 kD and a MWCO of between about 55 kD and about 110 kD as determined by dextran sieving before blood contact of the membrane.

3. The method of treating restless leg syndrome (RLS) according to claim 1, wherein the patient fulfills the International Restless Legs Syndrome Study Group (IRLSSG) consensus criteria.

4. The method of treating restless leg syndrome (RLS) according to claim 1, wherein the patient has a IRLS score of 11-20 (moderate), 21-30 (severe) or 31-40 (very severe).

5. The method of treating restless leg syndrome (RLS) according to claim 1, wherein the patient has a IRLS score of 11-20 (moderate).

6. The method of treating restless leg syndrome (RLS) according to claim 1, wherein the patient has a IRLS score of 21-30 (severe).

7. The method of treating restless leg syndrome (RLS) according to claim 1, wherein the patient has a IRLS score of 31-40 (very severe).

8. The method of treating restless leg syndrome (RLS) according to claim 1, wherein the patient receives concomitant medication with a dopamine agonist.

9. The method of treating restless leg syndrome (RLS) according to claim 8, wherein the dopamine agonist is Rotigotine.

10. The method of treating restless leg syndrome (RLS) according to claim 8, wherein the dopamine agonist is ropinirole.

11. The method of treating restless leg syndrome (RLS) according to claim 8, wherein the dopamine agonist is levodopa.

12. The method of treating restless leg syndrome (RLS) according to claim 1, wherein the patient is a hemodialysis patient.

13. The method of treating restless leg syndrome (RLS) according to claim 1, wherein the average effective pore size (radius) on the selective layer of the membrane as derived from the MWCO based on dextran sieving is above about 5.0 nm and below about 7.0 nm.

14. The method of treating restless leg syndrome (RLS) according to claim 2, wherein the average effective pore size (radius) on the selective layer of the membrane as derived from the MWCO based on dextran sieving is above about 5.0 nm and below about 7.0 nm.

15. The method of treating restless leg syndrome (RLS) according to claim 1, wherein the inner diameter of the membrane is below about 200 μm and the wall thickness is below about 40 μm.

16. The method of treating restless leg syndrome (RLS) according to claim 2, wherein the inner diameter of the membrane is below about 200 μm and the wall thickness is below about 40 μm.

17. The method of treating restless leg syndrome (RLS) according to claim 1, wherein the membrane is comprised in a fiber bundle which has a packing density of from about 53% to about 60% and wherein the fiber bundle comprises at least 80% crimped fibers.

18. The method of treating restless leg syndrome (RLS) according to claim 2, wherein the membrane is comprised in a fiber bundle which has a packing density of from about 53% to about 60% and wherein the fiber bundle comprises at least 80% crimped fibers.

19. The method of treating restless leg syndrome (RLS) according to claim 1, wherein the membrane is comprised in a fiber bundle which has a packing density of from about 53% to about 60% and wherein the fiber bundle consists of at least 80% crimped fibers.

20. The method of treating restless leg syndrome (RLS) according to claim 2, wherein the membrane is comprised in a fiber bundle which has a packing density of from about 53% to about 60% and wherein the fiber bundle consists of at least 80% crimped fibers.

* * * * *